(12) United States Patent
Kramer et al.

(10) Patent No.: US 9,724,075 B2
(45) Date of Patent: Aug. 8, 2017

(54) BIOPSY METHOD AND APPARATUS

(71) Applicants: Radu Kramer, Woodcliff Lake, NJ (US); Liviu Popa-Simil, Los Alamos, NM (US); Arthur Jacob, Hackensack, NJ (US)

(72) Inventors: Radu Kramer, Woodcliff Lake, NJ (US); Liviu Popa-Simil, Los Alamos, NM (US); Arthur Jacob, Hackensack, NJ (US)

(73) Assignee: Variable Guage Catheter Inc., Woodcliff Lake, NJ (US)

(*) Notice: Subject to any disclaimer, the term of this patent is extended or adjusted under 35 U.S.C. 154(b) by 0 days.

(21) Appl. No.: 15/261,087

(22) Filed: Sep. 9, 2016

(65) Prior Publication Data
US 2016/0374649 A1 Dec. 29, 2016

Related U.S. Application Data

(63) Continuation-in-part of application No. 14/164,762, filed on Jan. 27, 2014.
(Continued)

(51) Int. Cl.
*A61B 10/00* (2006.01)
*A61B 10/02* (2006.01)
(Continued)

(52) U.S. Cl.
CPC ........ *A61B 10/0275* (2013.01); *A61B 5/0075* (2013.01); *A61B 5/6848* (2013.01);
(Continued)

(58) Field of Classification Search
CPC ................ A61B 90/39; A61B 10/0233; A61B 2090/3908
(Continued)

(56) References Cited

U.S. PATENT DOCUMENTS

| 5,487,392 | A | | 1/1996 | Haaga |
| 6,056,700 | A | * | 5/2000 | Burney ................. A61B 90/39 600/564 |

(Continued)

*Primary Examiner* — Max Hindenburg
*Assistant Examiner* — Jonathan M Foreman
(74) *Attorney, Agent, or Firm* — Arthur Jacob

(57) ABSTRACT

A tissue sampling apparatus and method obtain a sample of tissue from a selected site and place a hemostatic plug at the selected site. The apparatus includes an external needle and an internal needle within the external needle. A chamber in the internal needle is divided by a divider member into a plug compartment for receiving a hemostatic plug, and a sample compartment for receiving a tissue sample. The divider member is resiliently biased into the plug compartment and the internal needle is movable relative to the external needle for admitting the hemostatic plug into the plug compartment and displacing the divider member into the sample compartment, and then closing the chamber. The apparatus then is advanced to the selected site where relative movement between the internal and external needles opens the chamber, allowing the divider member to expel the hemostatic plug from the plug compartment, and admitting a tissue sample into the sample compartment. Subsequent relative movement between the internal and external needles cuts the tissue sample from the surrounding tissue for removal from the selected site upon removal of the apparatus, while the expelled hemostatic plug remains at the site.

23 Claims, 6 Drawing Sheets

Related U.S. Application Data

(60) Provisional application No. 61/762,582, filed on Feb. 8, 2013.

(51) Int. Cl.
*A61B 17/12* (2006.01)
*A61B 5/00* (2006.01)
*A61B 5/06* (2006.01)
*A61B 5/145* (2006.01)

(52) U.S. Cl.
CPC .... *A61B 10/0283* (2013.01); *A61B 17/12013* (2013.01); *A61B 5/061* (2013.01); *A61B 5/14539* (2013.01); *A61B 2010/0208* (2013.01); *A61B 2017/12004* (2013.01); *A61B 2562/0233* (2013.01)

(58) Field of Classification Search
USPC .................................................. 600/564–568
See application file for complete search history.

(56) References Cited

U.S. PATENT DOCUMENTS

| | | | |
|---|---|---|---|
| 6,350,244 B1 * | 2/2002 | Fisher | A61B 90/39 600/562 |
| 6,770,070 B1 | 8/2004 | Balbierz | |
| 2006/0258955 A1 * | 11/2006 | Hoffman | A61B 10/06 600/564 |
| 2007/0106176 A1 | 5/2007 | Mark et al. | |
| 2010/0081964 A1 | 4/2010 | Mark et al. | |
| 2014/0228661 A1 * | 8/2014 | Popa-Simil | A61B 10/0275 600/361 |

* cited by examiner

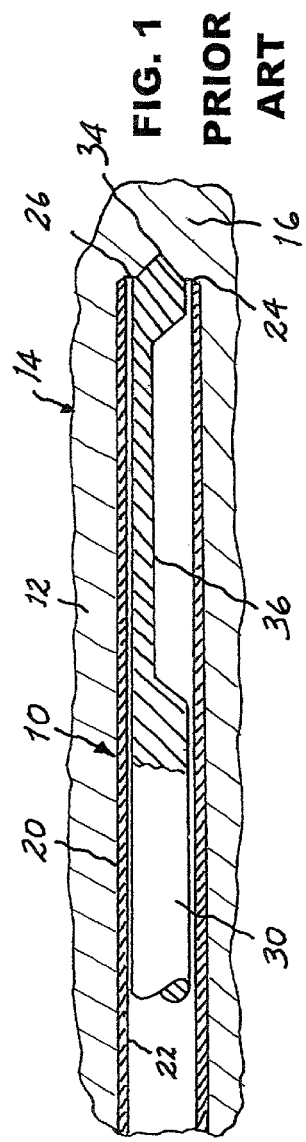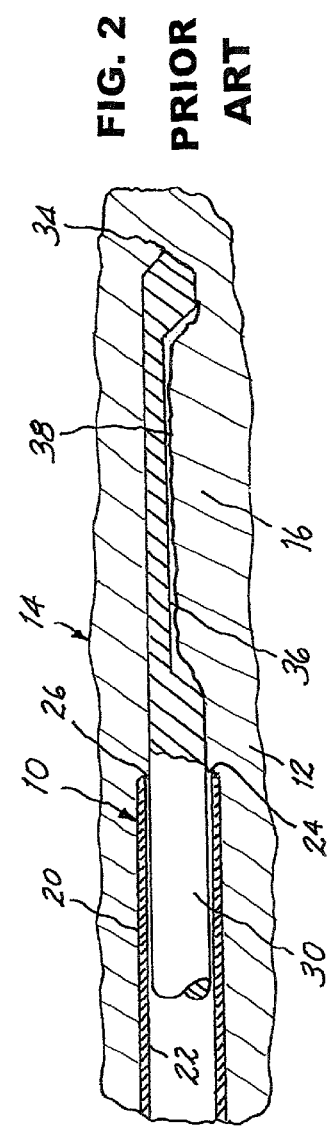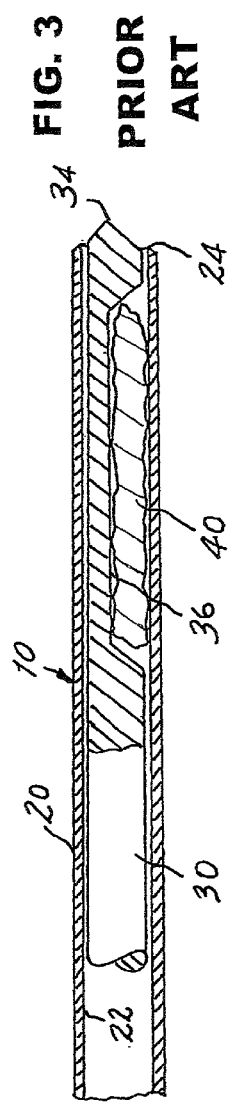

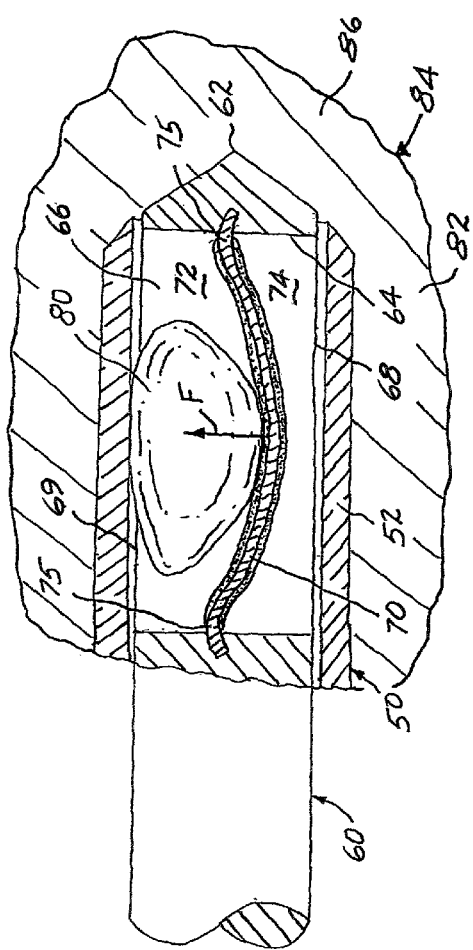
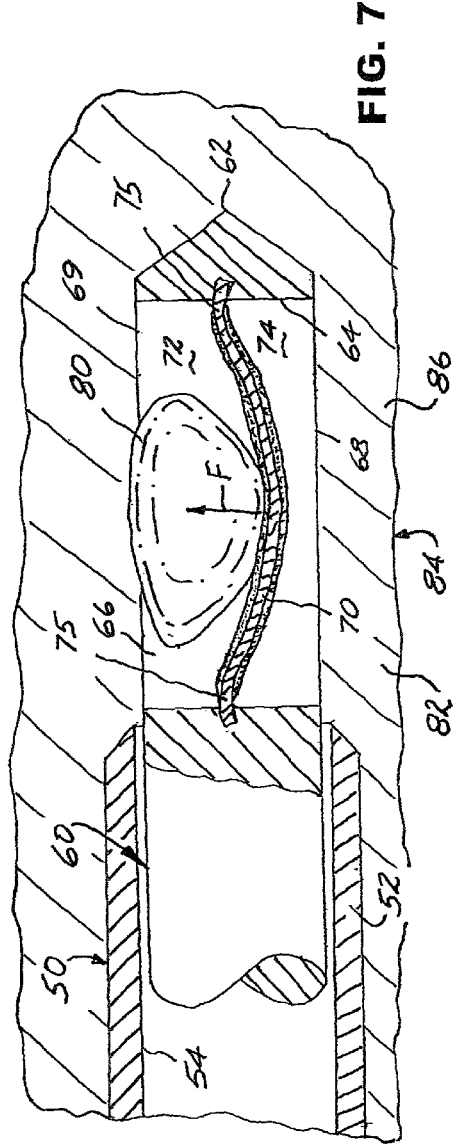

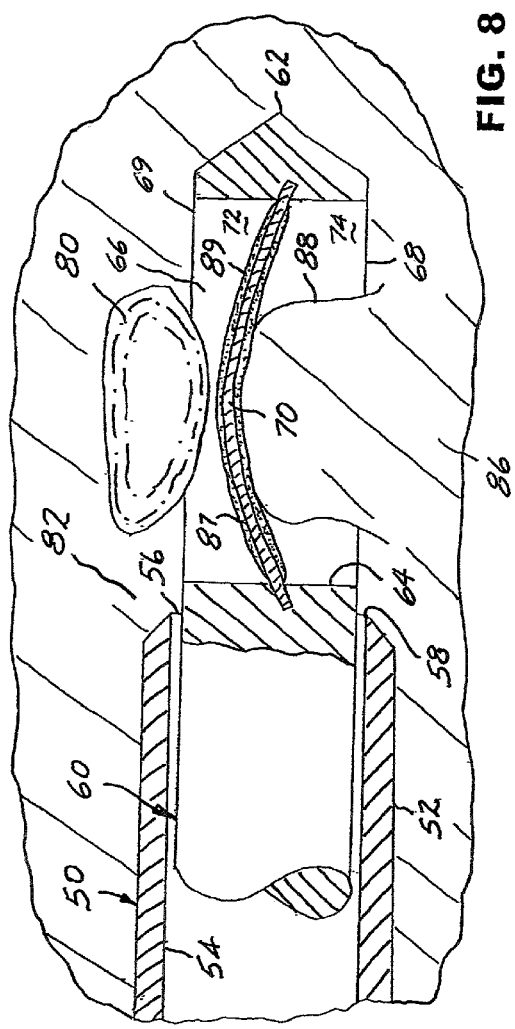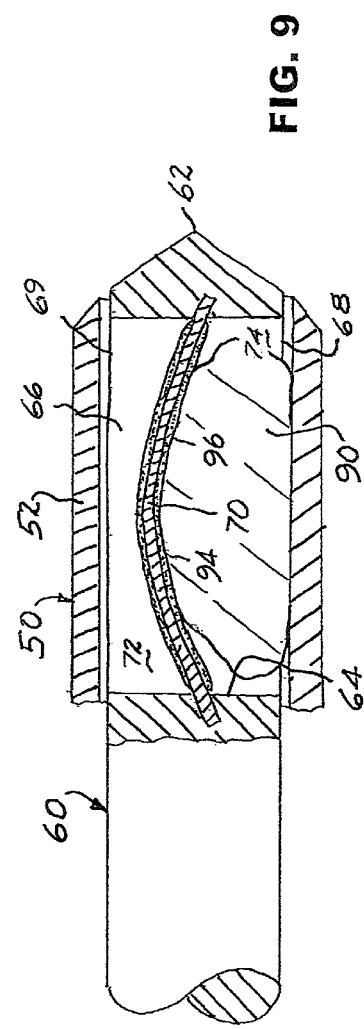

BIOPSY METHOD AND APPARATUS

This application is a continuation-in-part of application Ser. No. 14/164,762, filed Jan. 27, 2014, which claims the benefit of U.S. Provisional Application No. 61/762,582, filed Feb. 8, 2013, the disclosures of which are incorporated herein by reference thereto.

A biopsy is a medical procedure to acquire tissue for pathological examination. Ordinarily, a biopsy involves the removal of tissue from a living subject to determine the presence or extent of disease. The tissue generally is examined microscopically by a pathologist, and also can be analyzed chemically. When an entire lump or suspicious area is removed, the procedure is called an excisional biopsy. When only a sample of tissue is removed with preservation of the histological architecture of the tissues cells, the procedure is called an incisional biopsy or core biopsy. When a sample of tissue or fluid is removed with a needle in such a way that cells are removed without preserving the histological architecture of the tissue cells, the procedure is called a needle aspiration biopsy.

Actual tissue sampling often is done percutaneously with a long and fairly large bore needle designed for tissue removal, attached to a syringe or a more elaborate apparatus known as a "biopsy gun." The needle apparatus usually is passed several times through surrounding tissue at a selected site to remove several tissue samples. Percutaneous needle biopsies often are done using x-ray (usually CT) or ultrasound techniques to guide a surgeon to the selected site.

An open biopsy is a surgical procedure done in an operating room or outpatient surgical area using local or general anesthesia. The surgeon cuts into the organ being sampled and removes tissue under direct visualization using a needle or excision. A closed endoscopic biopsy uses a much smaller surgical cut than an open biopsy. A camera-like instrument attached to a flexible or rigid hollow tubing can be inserted, guided to the organ in question, and samples taken by needle or small cutting devices operated remotely.

The present invention provides a tissue sampling apparatus and method for obtaining a sample of tissue from a selected site while simultaneously placing a hemostatic plug at the selected site. As such, the present invention attains several objects and advantages, some of which are summarized as follows: Significantly reduces the effects of tissue penetration and rupture during a biopsy procedure; facilitates the removal of a tissue sample from a selected site and the placement of a resorbable and fully compatible hemostatic plug at the site; reduces traumatic effects that otherwise might occur during a biopsy procedure; simplifies the acquisition of a tissue sample from an accurately located selected site and the effective placement of a hemostatic plug at the selected site; reduces the time involved in a biopsy procedure; reduces any discomfort that might be experienced by a patient during a biopsy procedure; enhances the ability of a surgeon to quickly obtain a desired tissue sample from a selected site and place a hemostatic plug at the site; reduces bleeding at the site; reduces the risk of migration of any abnormal cells away from the site.

The above objects and advantages, as well as further objects and advantages, are attained by the present invention which may be described briefly as a tissue sampling apparatus for obtaining a sample of tissue from a selected site and for placing a hemostatic plug at the selected site, the apparatus comprising: an external needle having an internal passage and a tissue-cutting edge; an internal needle within the internal passage, the internal needle terminating at a forward tissue-penetrating tip and having a chamber adjacent the tissue-penetrating tip, the internal needle and the external needle being selectively movable relative to one another between a first position, wherein the chamber is closed by the external needle, and a second position, wherein the chamber is open; a divider member dividing the chamber into opposite compartments, including a plug compartment for receiving a hemostatic plug, and a sample compartment for receiving a tissue sample, the divider member being movable for displacement from within one to within the other of the opposite plug and sample compartments; and a biasing mechanism enabling displacement of the divider member into the sample compartment for accommodating a hemostatic plug within the plug compartment, when the plug compartment is closed by the external needle, and effecting displacement of the divider member out of the sample compartment and into the plug compartment for expelling the hemostatic plug out of the plug compartment and for admitting a tissue sample from surrounding tissue into the sample compartment upon opening the plug compartment; whereby, upon subsequent relative movement between the internal needle and the external needle to place the internal needle and the external needle into the first position, the tissue sample within the sample compartment will be cut from the surrounding tissue for removal upon removal of the tissue sample apparatus from the selected site, while the expelled hemostatic plug will remain at the site.

In addition, the present invention provides a tissue sampling method for obtaining a sample of tissue from a selected site and for placing a hemostatic plug at the selected site, the method comprising: providing an external needle with an internal passage and a tissue-cutting edge; providing an internal needle within the internal passage of the external needle, with the internal needle terminating at a forward tissue-penetrating tip and having a chamber adjacent the tissue-penetrating tip, the internal needle and the external needle being movable relative to one another between a first position, wherein the chamber is closed by the external needle and a second position, wherein the chamber is open; providing a divider member dividing the chamber into opposite compartments, including a plug compartment and a sample compartment, and a biasing mechanism providing a biasing force for biasing the divider member into the plug compartment; displacing the divider member out of the plug compartment and into the sample compartment, against the biasing force; placing a hemostatic plug into the plug compartment; with the internal needle and the external needle in the first position, and the hemostatic plug in the plug compartment, inserting the external needle into surrounding tissue at the selected site; subsequent to inserting the external needle and the internal needle into the surrounding tissue at the selected site, placing the internal needle and the external needle into the second position, thereby opening the chamber to enable displacement of the divider member, by the biasing force, into the plug compartment and concomitant expulsion of the hemostatic plug out of the plug compartment and into the surrounding tissue at the selected site, and reception of a sample of the surrounding tissue within the sample compartment; and subsequently placing the internal needle and the external needle into the first position, thereby cutting the sample of the surrounding tissue received within the sample compartment from the surrounding tissue for removal of a tissue sample upon removal of the external needle and internal needle from the selected site, while the expelled hemostatic plug remains at the site.

The invention will be understood more fully, while still further objects and advantages will become apparent, in the following detailed description of preferred embodiments of the invention illustrated in the accompanying drawing, in which:

FIG. 1 is a largely diagrammatic longitudinal cross-sectional view of a conventional biopsy needle inserted into a selected site in accordance with the prior art;

FIG. 2 is a largely diagrammatic longitudinal cross-sectional view similar to FIG. 1 and showing the biopsy needle in another stage of operation;

FIG. 3 is a largely diagrammatic longitudinal cross-sectional view similar to FIG. 1 and showing the biopsy needle in still another stage of operation;

FIG. 6 is a somewhat diagrammatic longitudinal cross-sectional view showing the tissue sampling apparatus in another stage of operation;

FIG. 7 is a somewhat diagrammatic longitudinal cross-sectional view showing the apparatus in still another stage of operation;

FIG. 8 is a somewhat diagrammatic longitudinal cross-sectional view similar to FIG. 7 and showing the apparatus in yet another stage of operation;

FIG. 9 is a somewhat diagrammatic longitudinal cross-sectional view showing the apparatus in another stage of operation;

Figure 4:
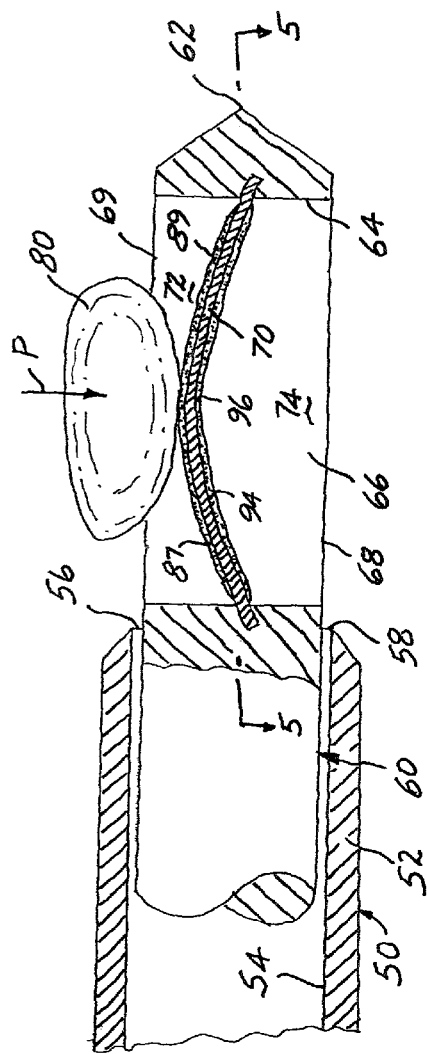
FIG. 4 is a somewhat diagrammatic longitudinal cross-sectional view of a tissue sampling apparatus constructed in accordance with the present invention showing the apparatus being prepared for use in accordance with a method of the present invention.
Figure 5:
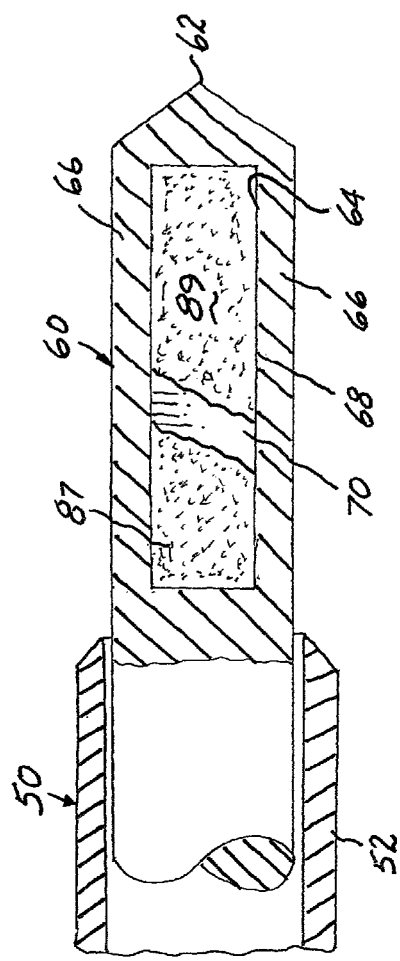
FIG. 5 is a fragmentary cross-sectional view taken along line 5-5 of FIG. 4.

Referring now to the drawing, and especially to FIGS. 1 through 3 thereof, a conventional biopsy needle 10 is shown inserted into surrounding tissue 12 at a selected site 14 wherein there is tissue 16 to be sampled during the conduct of a biopsy procedure. Biopsy needle 10 includes an external needle 20 having an internal passage 22 and a tissue-cutting edge 24 at the forward end 26 of the external needle 20. An internal needle 30 extends longitudinally within the passage 22 of external needle 20 and terminates at a forward tissue-penetrating tip 34. A recess 36 within internal needle 30 is located adjacent the tissue-penetrating tip 34 and extends longitudinally along internal needle 30 and laterally across a portion of the internal needle 30.

With the forward end 26 of the external needle 20 placed in juxtaposition with the tissue 16 to be sampled, as seen in FIG. 1, the internal needle 30 is advanced relative to the external needle 20 to enter the tissue 16, as seen in FIG. 2, allowing a portion 38 of tissue 16 to enter recess 36. Then, external needle 20 is moved forward over internal needle 30, as seen in FIG. 3, causing tissue-cutting edge 24 to sever a tissue sample 40 from tissue 16 and capture of the severed tissue sample 40 within recess 36 for subsequent delivery of the sample 40, upon removal of the biopsy needle 10 from site 14, for examination of the sample 40, all in accordance with now conventional procedure.

Turning now to FIGS. 4 through 9, a tissue sampling apparatus constructed in accordance with the present invention is shown at 50 and is seen in an initial stage of operation in accordance with a method of the present invention. Apparatus 50 is seen to include an external needle 52 having a generally tubular construction including a longitudinally extending internal passage 54 terminating at a forward end 56. As is now conventional, a tissue-cutting edge 58 is located at the forward end 56. An internal needle 60 extends longitudinally within passage 54 and terminates at a forward tissue-penetrating tip 62.

Apparatus 50 includes a chamber, shown in the form of a slot 64, passing laterally through the internal needle 60, adjacent the tip 62, bounded transversely by opposite side walls 66 and having a sample portal 68 and a plug portal 69, provided for purposes to be described more fully below. Internal needle 60 and external needle 52 are selectively movable relative to one another, in apparatus 50 internal needle 60 being movable between an advanced position, wherein slot 64 is open, outside of external needle 52, as seen in FIG. 4, and a retracted position, wherein slot 64 is closed by external needle 52, as seen in FIG. 6. A divider member is shown in the form of leaf spring 70 located within the slot 64 to divide the slot into a plug compartment 72 and a laterally opposite sample compartment 74. The leaf spring 70 is shown in FIG. 4 bowed into the plug compartment 72, the bowed configuration having resiliently flexible sections 75, shown flexed in FIGS. 6 and 7, serving as a biasing mechanism enabling selective displacement of the leaf spring 70 out of the plug compartment 72 and into the sample compartment 74, as illustrated in connection with FIGS. 6 and 7, with a biasing force F in a direction biasing the leaf spring back toward the plug compartment 72, as seen in FIGS. 4, 8 and 9.

With the internal needle 60 in the advanced position and the slot 64 exposed, as illustrated in FIG. 4, a hemostatic plug 80 is inserted through plug portal 69 to be placed within plug compartment 72, pushing with a force P to displace the leaf spring 70 into the sample compartment 74, while flexing sections 75, thereby establishing the biasing force F. The internal needle 60 then is retracted into the external needle 52 to close the slot 64, with the plug 80 captured within plug compartment 72, and the apparatus 50 is inserted into surrounding tissue 82 until the apparatus 50 is placed at a selected site 84, in juxtaposition with tissue 86 to be harvested for examination, all as illustrated in FIG. 6.

Then, internal needle 60 is moved to the advanced position illustrated in FIG. 7, thereby opening plug portal 69 of slot 64 and exposing plug 80 to surrounding tissue 82. With the slot 64 thus open, biasing force F will actuate leaf spring 70 to move out of sample compartment 74 and into plug compartment 72, thereby expelling plug 80 through plug portal 69 and into surrounding tissue 82, as seen in FIG. 8. In order to facilitate expulsion of plug 80, leaf spring 70 advantageously includes a hydrophobic coating 87 located to provide a hydrophobic surface 89 confronting the plug compartment 72. At the same time, a portion 88 of tissue 86 enters sample compartment 74, through sample portal 68, assisted by being drawn into sample compartment 74 by the movement of leaf spring 70 out of the sample compartment 74, which movement creates a suction within sample compartment 74 to facilitate drawing surrounding tissue into sample compartment 74 and essentially filling the sample compartment 74 with portion 88 of tissue 86, thereby maximizing the volume of harvested tissue, all as seen in FIG. 8.

Once the portion 88 of tissue 86 is situated within sample compartment 74, external needle 52 is advanced over internal needle 60 so that tissue-cutting edge 58 cuts a tissue sample 90 from the tissue 86 and the severed tissue sample 90 is captured within sample compartment 74, as seen in FIG. 9. The entire apparatus 50 then is removed from the surrounding tissue 82 and the sample 90 is delivered for examination, while the plug 80 remains at the site 84. Hemostatic plug 80 serves to reduce bleeding at the site 84. A the same time, plug 80 reduces the risk of migration away from site 84 of any abnormal cells that might be present at site 84.

In order to maximize the volume of sample 90 drawn into sample compartment 74, leaf spring 70 advantageously includes a hydrophilic coating 94 located to provide a hydrophilic surface 96 confronting the sample compartment 74, thereby enhancing the ability quickly to fill sample compartment 74. In this manner, a tissue sample 90 is obtained from a selected site 84 and hemostatic plug 80 is placed at the site of the removal, all in a single, simultaneous operation.

Figure 10:
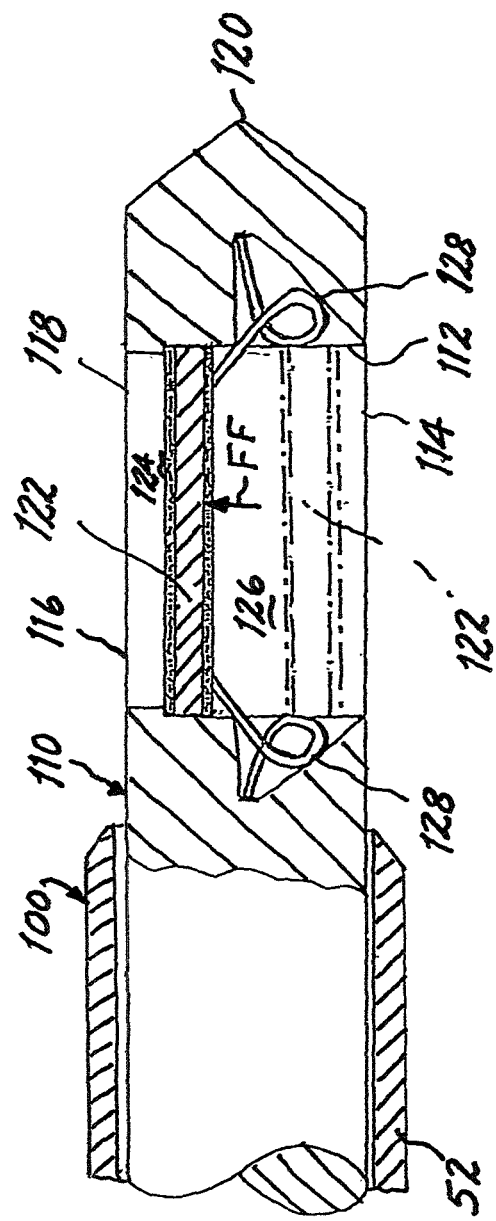
FIG. 10 is a somewhat diagrammatic longitudinal cross-sectional view part showing another embodiment of the present invention.

Turning now to FIG. 10, wherein like elements are labeled with the same reference characters as in the embodiment illustrated in FIGS. 4 through 9, in an alternate apparatus 100, internal needle 60 has been replaced by internal needle 110 having a chamber in the form of a slot 112 passing laterally through the internal needle 110, between a sample portal 114 and a plug portal 116, bounded transversely by opposite side walls 118 extending longitudinally toward adjacent tissue-penetrating tip 120. A divider member in the form of a substantially rigid partition 122 divides the slot 112 into a plug compartment 124 and a sample compartment 126, and a biasing mechanism includes coil springs 128 coupled to the partition 122 for establishing a biasing force FF biasing the partition 122 from a position within the sample compartment 126, as illustrated in phantom, to a position within the plug compartment 124, as shown in full lines. The use and operation of apparatus 100 is as described above in connection with apparatus 50.

Figure 11:
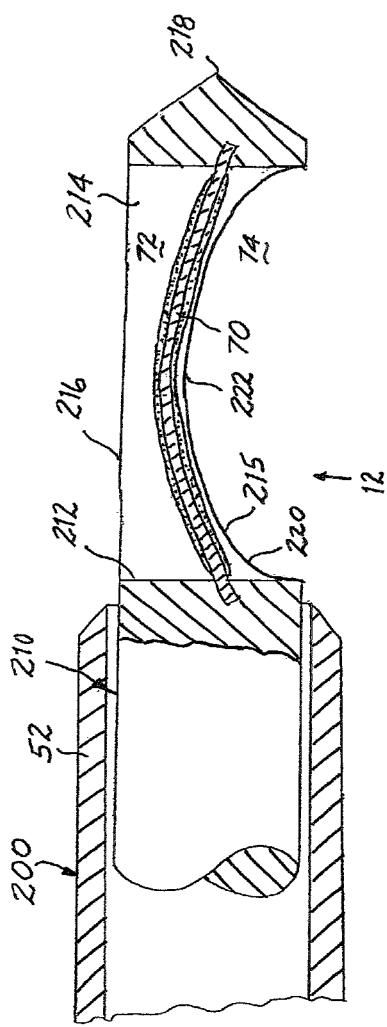
FIG. 11 is a somewhat diagrammatic longitudinal cross-sectional view showing still another embodiment of the present invention.
Figure 12:
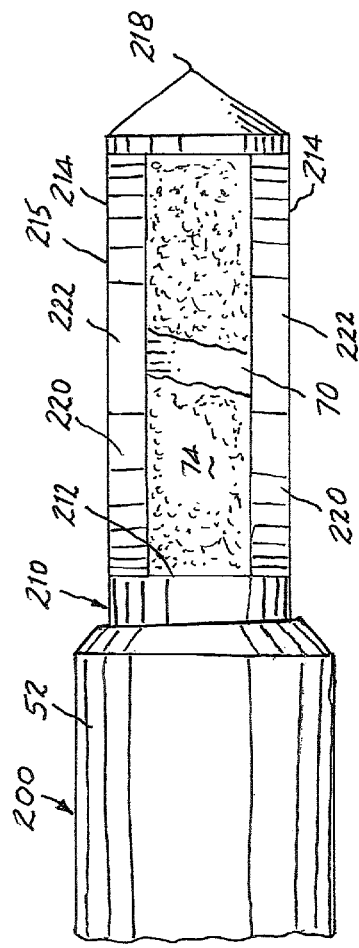
FIG. 12 is a somewhat diagrammatic plan view taken in the direction of arrow 12 in FIG. 11.

Another embodiment, illustrated in FIGS. 11 and 12, is in the form of apparatus 200 wherein like elements are labeled with the same reference characters as in the embodiment illustrated in FIGS. 4 through 9. Here, internal needle 60 has been replaced by internal needle 210 having a chamber in the form of a slot 212 passing laterally through the internal needle 210 and located between transversely opposite side walls 214 extending laterally between a sample portal 215 and a plug portal 216, longitudinally toward adjacent tissue-penetrating tip 218.

As in the embodiment described in connection with apparatus 50, leaf spring 70 divides the chamber into plug compartment 72 and laterally opposite sample compartment 74. However, in apparatus 210, side walls 214 are provided with a recessed configuration, as depicted by arched portions 220 extending laterally to provide transversely opposite openings 222 into sample compartment 74 when internal needle 210 is in the illustrated advanced position. In this manner, the movement of surrounding tissue into sample compartment 74 is enhanced by enabling entry of tissue into sample compartment 74 through openings 222 in side walls 214, as well as through sample portal 215, to maximize the volume of tissue drawn into sample compartment 74 and rapidly to pass the drawn tissue into sample compartment 74 to quickly fill sample compartment with a greater volume of tissue to be harvested.

It will be seen that the present invention attains all of the objects and advantages summarized above, namely: Significantly reduces the effects of tissue penetration and rupture during a biopsy procedure; facilitates the removal of a tissue sample from a selected site and the placement of a resorbable and fully compatible hemostatic plug at the site; reduces traumatic effects that otherwise might occur during a biopsy procedure; simplifies the acquisition of a tissue sample from an accurately located selected site and the effective placement of a hemostatic plug at the selected site; reduces the time involved in a biopsy procedure; reduces any discomfort that might be experienced by a patient during a biopsy procedure; enhances the ability of a surgeon to quickly obtain a desired tissue sample from a selected site and place a hemostatic plug at the site; reduces bleeding at the site; reduces the risk of migration of any abnormal cells away from the site.

The above detailed description of preferred embodiments of the invention is provided by way of example only. Various details of design, construction and procedure may be modified without departing from the true spirit and scope of the present invention, as set forth in the appended claims.

The embodiments of the invention in which an exclusive property or privilege is claimed are defined as follows:

1. A tissue sampling apparatus for obtaining a sample of tissue from a selected site and for placing a hemostatic plug at the selected site, the apparatus comprising:
   an external needle having an internal passage and a tissue-cutting edge;
   an internal needle within the internal passage, the internal needle terminating at a forward tissue-penetrating tip and having a chamber adjacent the tissue-penetrating tip, the internal needle and the external needle being selectively movable relative to one another between a first position, wherein the chamber is closed by the external needle, and a second position, wherein the chamber is open;
   a divider member dividing the chamber into opposite compartments, including a plug compartment for receiving a hemostatic plug, and a sample compartment for receiving a tissue sample, the divider member being movable for displacement from within one to within the other of the opposite plug and sample compartments; and
   a biasing mechanism enabling displacement of the divider member into the sample compartment for accommodating a hemostatic plug within the plug compartment, when the plug compartment is closed by the external needle, and effecting displacement of the divider member out of the sample compartment and into the plug compartment for expelling the hemostatic plug out of the plug compartment and for drawing a tissue sample from surrounding tissue into the sample compartment upon opening the plug compartment;
   whereby, upon subsequent relative movement between the internal needle and the external needle to place the internal needle and the external needle into the first position, the tissue sample within the sample compartment will be cut from the surrounding tissue for removal upon removal of the tissue sample apparatus from the selected site, while the expelled hemostatic plug will remain at the site.

2. The tissue sampling apparatus of claim 1 wherein:
   the internal passage extends longitudinally within the external needle and terminates at a forward end, and the tissue-cutting edge is located at the forward end; and
   the chamber is located longitudinally adjacent the tissue-penetrating tip such that the first position comprises a retracted position, wherein the chamber is closed by the external needle and the tissue-penetrating tip is juxtaposed with the tissue-cutting edge, and the second position comprises an advanced position, wherein the tissue-penetrating tip is spaced longitudinally forward of the tissue-cutting edge and the chamber is open.

3. The tissue sampling apparatus of claim 2 wherein the divider member is placed to locate the plug compartment laterally opposite the sample compartment.

4. The tissue sampling apparatus of claim 3 wherein the divider member comprises a leaf spring biased for resilient displacement from the sample compartment into the plug compartment.

5. The tissue sampling apparatus of claim 3 wherein the biasing member comprises at least one spring member coupled with the divider member for resiliently biasing the divider member from the sample compartment into the plug compartment.

6. The tissue sampling apparatus of claim 3 wherein the chamber comprises a slot extending through the internal needle between a sample portal and a plug portal.

7. The tissue sampling apparatus of claim 3 wherein the slot is bounded by opposite side walls extending laterally between the sample portal and the plug portal, the side walls including side openings communicating with the sample compartment for admitting surrounding tissue into the sample compartment.

8. The tissue sampling apparatus of claim 7 wherein the divider member comprises a leaf spring biased for resilient displacement from the sample compartment into the plug compartment.

9. The tissue sampling apparatus of claim 7 wherein the biasing member comprises at least one spring member coupled with the divider member for resiliently biasing the divider member from the sample compartment into the plug compartment.

10. The tissue sampling apparatus of claim 1 wherein the divider member comprises a leaf spring biased for resilient displacement from the sample compartment into the plug compartment.

11. The tissue sampling apparatus of claim 1 wherein the biasing member comprises at least one spring member coupled with the divider member for resiliently biasing the divider member from the sample compartment into the plug compartment.

12. The tissue sampling apparatus of claim 1 wherein the chamber comprises a slot extending through the internal needle between a sample portal and a plug portal.

13. The tissue sampling apparatus of claim 12 wherein the slot is bounded by opposite side walls extending laterally between the sample portal and the plug portal, the side walls including side openings communicating with the sample compartment for admitting surrounding tissue into the sample compartment.

14. The tissue sampling apparatus of claim 12 wherein divider member comprises a leaf spring biased for resilient displacement from the sample compartment into the plug compartment.

15. The tissue sampling apparatus of claim 12 wherein the biasing member comprises at least one spring member coupled with the divider member for resiliently biasing the divider member from the sample compartment into the plug compartment.

16. The tissue sampling apparatus of claim 1 wherein the divider member includes hydrophobic surface confronting the plug compartment.

17. The tissue sampling apparatus of claim 1 wherein the divider member includes a hydrophilic surface confronting the sample compartment.

18. The tissue sampling apparatus of claim 1 wherein the divider member includes a hydrophobic surface confronting the plug compartment and a hydrophilic surface confronting the sample compartment.

19. The tissue sampling apparatus of claim 18 wherein the divider member comprises a leaf spring biased for resilient displacement from the sample compartment into the plug compartment.

20. The tissue sampling apparatus of claim 18 wherein the biasing member comprises at least one spring member coupled with the divider member for resiliently biasing the divider member from the sample compartment into the plug compartment.

21. A tissue sampling method for obtaining a sample of tissue from a selected site and for placing a hemostatic plug at the selected site, the method comprising:
providing an external needle with an internal passage and a tissue-cutting edge;
providing an internal needle within the internal passage of the external needle, with the internal needle terminating at a forward tissue-penetrating tip and having a chamber adjacent the tissue-penetrating tip, the internal needle and the external needle being movable relative to one another between a first position, wherein the chamber is closed by the external needle and a second position, wherein the chamber is open;
providing a divider member dividing the chamber into opposite compartments, including a plug compartment and a sample compartment, and a biasing mechanism providing a biasing force for biasing the divider member into the plug compartment;
displacing the divider member out of the plug compartment and into the sample compartment, against the biasing force;
placing a hemostatic plug into the plug compartment;
with the internal needle and the external needle in the first position, and the hemostatic plug in the plug compartment, inserting the external needle into surrounding tissue at the selected site;
subsequent to inserting the external needle and the internal needle into the surrounding tissue at the selected site, placing the internal needle and the external needle into the second position, thereby opening the chamber to enable displacement of the divider member, by the biasing force, into the plug compartment and concomitant expulsion of the hemostatic plug out of the plug compartment and into the surrounding tissue at the selected site, and drawing of a sample of the surrounding tissue within the sample compartment; and
subsequently placing the internal needle and the external needle into the first position, thereby cutting the sample of the surrounding tissue received within the sample compartment from the surrounding tissue for removal of a tissue sample upon removal of the external needle and internal needle from the selected site, while the expelled hemostatic plug remains at the site.

22. The method of claim 21 wherein in the first position the internal needle is retracted within the external needle, and upon placing the internal needle and the external needle into the second position, the internal needle is advanced longitudinally relative to the external needle to open the chamber.

23. The method of claim 22 wherein in the second position the internal needle is advanced longitudinally out of the external needle, and placing the internal needle and the external needle into the first position moves the external needle over the internal needle to cut the sample of the surrounding tissue received within the sample compartment from the surrounding tissue.

* * * * *